United States Patent [19]

London

[11] Patent Number: Plant 6,874

[45] Date of Patent: Jun. 20, 1989

[54] SPATHIPHYLLUM NAMED — PHOENIX

[75] Inventor: Christopher J. London, Apopka, Fla.

[73] Assignee: Hoffman Plant Laboratories, Inc., Santa Paula, Calif.

[21] Appl. No.: 91,552

[22] Filed: Aug. 28, 1987

[51] Int. Cl.[4] ..... A01H 5/00

[52] U.S. Cl. ..... Plt./88

[58] Field of Search ..... Plt./88

*Primary Examiner*—James R. Feyrer

[57] ABSTRACT

A new and distinct cultivar of Spathiphyllum named Phoenix which is particularly distinguished by having a darker, glossier leaf, a rounder, shorter, thicker and stiffer leaf blade and a larger, earlier-flowering bloom than Spathiphyllum Supreme. The cultivar was discovered in the progeny of self-pollinated Spathiphyllum St. Mary. The cultivar is shorter than the parent Spathiphyllum St. Mary, has smaller, rounder and thicker leaves than St. Mary, and is darker green than St. Mary.

1 Drawing Sheet

The new cultivar is a product of a planned breeding program carried out by Christopher London, New Gene Research and Development, Incorporated, Apopka, Fla. The parents are Spathiphyllum St. Mary (seed parent) and Spathiphyllum St. Mary (pollen parent). The cultivar named Phoenix was arrived at through a self-pollination of Spathiphyllum St. Mary. The cultivar is shorter than the parent Spathiphyllum St. Mary, has smaller, rounder and thicker leaves than St. Mary, and is darker green than St. Mary. The cultivar was discovered from the progeny of the stated cross by Mr. London. Asexual propagation by tissue culture was used to increase the number of plants for evaluation and to demonstrate the stability of the combination of characters from generation to generation.

The following observations, measurements and values describe plants grown in Apopka, Fla. under greenhouse conditions which closely approximate those generally used in horticultural practice.

The following traits have been repeatedly observed and have been repeatedly observed to be characteristics which in combination distinguish Spathiphyllum hybrida Phoenix from other Spathiphyllum of the same general type, i.e. Supreme.

DISTINCTIONS

1. Phoenix has a rounder, shorter leaf blade than Supreme.
2. Phoenix has a thicker, stiffer leaf blade than Supreme.
3. Phoenix appears shorter and more compact than Supreme.
4. Phoenix's blooms are larger than Supreme.
5. Phoenix flowers at a younger age than Supreme.
6. Phoenix suckers profusely after the first flower.
7. Phoenix has shinier, darker green leaves than Supreme.
8. Phoenix has primary veins on the leaf blade that are more articulated than Supreme.
9. Phoenix has a rounder flower than Supreme.

FIGURE

The appearance and distinctive character of Phoenix is shown in the FIGURE which is a true color photograph of the cultivar.

DESCRIPTION

All color references are measured against The Royal Horticultural Society Colour Chart.

Origin: Seedling.

Classification: Spathiphyllum hybrida.

Propagation: Asexual production either through tissue culture or division.

Plant: In a 21 cm pot, Phoenix will be at the mature size of approximately 0.5 meters to 0.7 meters in height and approximately 0.9 meters to 1.1 meters in width after approximately 75 weeks to 80 weeks under the appropriate growing conditions from tissue culture. On a mature plant of 2 years in a 21 cm pot, the following applies:

Leaves:

*Form.*—The leaf blade is ovate having cuspidate/acuminate tendencies and an obtuse/cordate base.

*Size.*—Leaf blades of a mature sized plant will be approximately 31 cm to 35 cm in length and approximately 18 cm to 21 cm in width.

*Petiole.*—The petiole will be approximately 45 cm to 55 cm in height from the base of the petiole to the base of the leaf blade on the primary shoot. Secondary shoots may be somewhat smaller depending on the age of the shoot. The petiole will be approximately 6 mm to 8 mm in diameter. The geniculum is prominent and lighter in color than the petiole.

*Texture.*—Leaves will be more glossy than Supreme. Leaves will be stiffer and thicker than Supreme.

*Veins.*—Veins are sunken deeply with the leaf blade somewhat concave between veins. Well defined veins on mature sized leaves are approximately 11 mm to 22 mm apart measured halfway between the midrib and leaf edge and do stand out prominently on the abaxial side. The veins are farther apart halfway between the tip and the base than nearer the tip or the base.

*Color.*—Expanded mature leaf: Adaxial side: 137A, 139A. Abaxial side: 191A, 138A. Abaxial veins: 144B, 144C, 145B. Expanding mature leaf: Adaxial side: Darker than 137A. Abaxial side: 191B, 138B. Abaxial veins: 144C.

INFLORESCENCE

Immature: The spathe is tightly rolled around the spadix and extrudes from the petiole sheath. The spathe is fully open approximately when the pedicel is fully elongated — approximately 0.85 meters to 0.95 meters from the soil surface.

Mature:

*Spathe.*—Size: The flattened spathe is approximately 15 cm to 19 cm high and approximately 9 cm to 13 cm in width. Color: The color is 155D.

Arrangement: The spathe stands up on straight wiry pedicles and opens above the leaves.

*Shape.*—The Spathe is ovate with an acute/acuminate apex that is straight. It is cupped and is approximately 16 cm to 18 cm high and 9 cm to 13 cm in width. It is 2 cm to 3 cm in depth.

Flowering time: After approximately 11 months to 12 months for an untreated plant depending on season, approximately 1 to 3 blossoms will be present. Smaller blossoms may occur on less mature growth.

REPRODUCTIVE ORGANS

Spadix:

*Size.*—Approximately 7 cm to 10 cm high and approximately 13 mm to 18 mm wide.

*Color.*—When the spathe unrolls, the spadix is 12D, 13D.

*Stamens.*—Anthers and filaments are not clearly visible.

*Pollen.*—158C in color.

*Pistle.*—12D, 13D in color, protruding between the staminate flowers, firmly fixed to the main axle. The pistilate flowers extend approximately 2.5 mm to 3.5 mm beyond the staminate flowers.

*Roots.*—White fleshy main roots with fine laterals.

General observation: Spathiphyllum Phoenix is a compact, dark green plant with round thick leaves. The first flowers are relatively large for most Spathiphyllum cultivars. As a 6" or 8" finished pot, it is clearly distinguishable from other Spathiphyllum cultivars by color, leaf shape, flower size, and plant habit.

The combination of characteristics described above established that Phoenix is a unique new cultivar.

I claim:

1. A new and distinct cultivar of Spathiphyllum as described and illustrated.

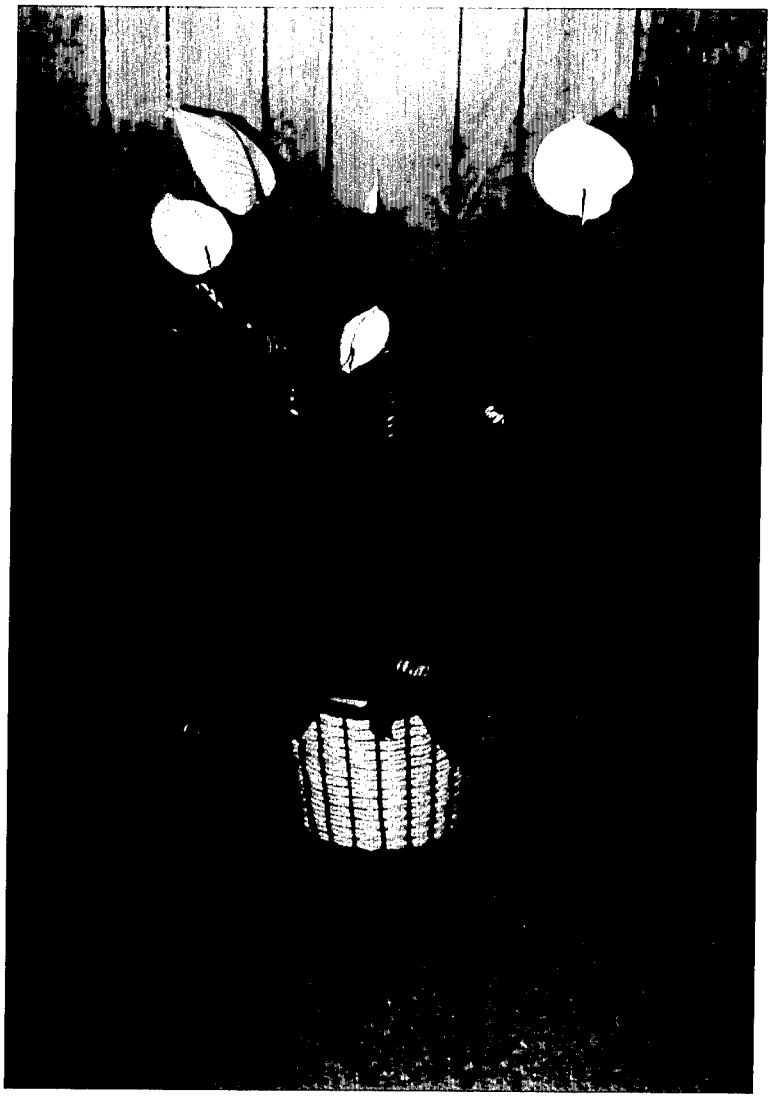

* * * * *